(12) United States Patent
Banta et al.

(10) Patent No.: US 10,519,469 B2
(45) Date of Patent: *Dec. 31, 2019

(54) METHODS AND SYSTEMS FOR PRODUCING PRODUCTS USING ENGINEERED SULFUR OXIDIZING BACTERIA

(71) Applicant: The Trustees of Columbia University in the City of New York, New York, NY (US)

(72) Inventors: Scott Banta, Fairfield, CT (US); Alan West, Tenafly, NJ (US); Timothy Kernan, Pawling, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 56 days.

This patent is subject to a terminal disclaimer.

(21) Appl. No.: 15/660,031

(22) Filed: Jul. 26, 2017

(65) Prior Publication Data

US 2018/0195090 A1 Jul. 12, 2018

Related U.S. Application Data

(63) Continuation of application No. 14/377,223, filed on Aug. 7, 2014, now Pat. No. 9,745,601.

(60) Provisional application No. 61/599,550, filed on Feb. 16, 2012.

(51) Int. Cl.
| | |
|---|---|
| *C12P 1/04* | (2006.01) |
| *C12M 1/00* | (2006.01) |
| *C12P 7/16* | (2006.01) |
| *C12N 1/20* | (2006.01) |
| *C12N 9/04* | (2006.01) |
| *C12N 9/88* | (2006.01) |
| *C12P 3/00* | (2006.01) |
| *C12P 5/02* | (2006.01) |
| *C12P 7/04* | (2006.01) |

(52) U.S. Cl.
CPC ............... *C12P 1/04* (2013.01); *C12M 21/12* (2013.01); *C12M 43/00* (2013.01); *C12N 1/20* (2013.01); *C12N 9/0006* (2013.01); *C12N 9/88* (2013.01); *C12P 3/00* (2013.01); *C12P 5/02* (2013.01); *C12P 7/04* (2013.01); *C12P 7/16* (2013.01); *Y02E 50/10* (2013.01)

(58) Field of Classification Search
None
See application file for complete search history.

(56) References Cited

U.S. PATENT DOCUMENTS

| | | | | |
|---|---|---|---|---|
| 7,687,161 B2 * | 3/2010 | Karamanev | ......... | H01M 4/8652 |
| | | | | 429/101 |
| 2009/0081746 A1 * | 3/2009 | Liao | ....................... | C12N 15/52 |
| | | | | 435/160 |
| 2010/0120104 A1 * | 5/2010 | Reed | ........................ | C12P 7/40 |
| | | | | 435/140 |

* cited by examiner

*Primary Examiner* — Paul J Holland
(74) *Attorney, Agent, or Firm* — Murtha Cullina LLP; Anthony P. Gangemi

(57) ABSTRACT

Methods and systems for producing a biofuel using genetically modified sulfur-oxidizing and iron-reducing bacteria (SOIRB) are disclosed. In some embodiments, the methods include the following: providing a SOIRB that have been genetically modified to include a particular metabolic pathway to enable them to generate a biofuel; feeding a first source of ferric iron to the SOIRB; feeding sulfur, water, and carbon dioxide to the SOIRB; producing at least the first particular biofuel, a first source of ferrous iron, sulfate, excess ferric iron, and an SOIRB biomass; electrochemically reducing the excess ferric iron to a second source of ferrous iron; providing an iron-oxidizing bacteria that have been genetically modified to include a particular metabolic pathway to enable them to generate a second biofuel; producing at least the second biofuel, a second source of ferric iron, and an IOB biomass; and feeding the second source of ferric iron to the SOIRB.

14 Claims, 5 Drawing Sheets

METHODS AND SYSTEMS FOR PRODUCING PRODUCTS USING ENGINEERED SULFUR OXIDIZING BACTERIA

CROSS REFERENCE TO RELATED APPLICATION(S)

This application is a continuation of U.S. Non-provisional patent application Ser. No. 14/377,223, filed Aug. 7, 2014, which claims the benefit of U.S. Provisional Application No. 61/599,550, filed Feb. 16, 2012, each of which is incorporated by reference as if disclosed herein in their entirety.

BACKGROUND

There has been interest in the development of liquid biofuels as these processes have the potential to directly fix carbon dioxide into transportation fuels, which is potentially carbon neutral and politically attractive. Cellulose based biofuels including bioethanol, algae-derived lipids, cyanobacteria, and algae derived hydrogen ($H_2$) are among the most studied biofuels. Despite the promise of these technologies and processes, there are specific limitations that preclude their wide-spread application. For example, post-processing of algal cells and derived lipids imposes higher production costs on algal biodiesel. The production rates of $H_2$ from cyanobacteria still remains low and productivity needs to be improved. Genetically engineered photosynthetic organisms have also been explored for bioethanol production. However separation of ethanol from the aqueous phase remains a challenge.

Microbial fuel cells have been under investigation and development for more than a century, as the use of cells to harvest electrical energy from waste streams is attractive for many reasons. In a biofuel cell, biological catalysts are used on an anode to oxidize biofuels, and a cathode is created that can use the generated electrons to reduce oxygen to water. These systems can either be microbial with living cells on the electrodes, or they can be enzymatic systems, with purified enzymes on the electrodes. In both designs, power can be generated from the oxidation of biofuels, and there are many advantages to these systems over conventional fuel cells and other power generation schemes. However, much research still needs to be done with microbial fuel cells to make them practical and cost-efficient. A significant limitation for both enzymatic and microbial fuel cells is the need for mediators to enable electrical contact between the biological components and inorganic electrode. In some microbial systems, these mediators are made by the organisms themselves, and in other technologies, synthetic mediators are added to the system. In some systems, cells must make physical contact with the electrodes for electron transfer. This can be a significant limitation as it reduces the cellular mass that can be used for biochemical conversion.

Natural gas is frequently purified from "sour gas", which is a natural gas deposit containing high volumes of sulfur or hydrogen sulfide. The separate sulfur compounds are a significant waste product produced by these processes, lacking an economical or sustainable disposal process.

SUMMARY

Living cells have the ability to reproduce and maintain their catalytic machinery, and their metabolic pathways can be rationally altered to meet desired process objectives. But, efficient electron transfer from the electrode to the organism can limit metabolic production, and the use of mediating species can result in a process that is not economically viable. One way to address these limitations is to explore alternative organisms that naturally utilize mediators that are more attractive. The disclosed subject matter includes the metabolic engineering of chemolitotrophic sulfur-oxidizing and iron-reducing bacteria (SOIRB), such as *Acidithiobacillus ferrooxidans*, to develop a process that can overcome these limitations. SOIRB have the natural ability to fix carbon dioxide while oxidizing sulfur and reducing ferric iron ($Fe^{3+}$) to ferrous iron ($Fe^{2+}$).

Aspects of the disclosed subject matter include the use of engineered strains of the SOIRB, e.g., *A. ferrooxidans*, for the production of biofuels. SOIRB fix carbon dioxide for cell-synthesis while deriving energy from the oxidation of sulfur and reduction of ferric iron to ferrous iron. The ferrous iron produced upon reduction of ferric iron can be electrochemically oxidized back to ferric iron in an electrochemical reactor, and additional ferric iron can be added from any ferric iron-rich stream. In this way, the SOIRB can be grown efficiently in a bioreactor using ferric iron as the mediator.

BRIEF DESCRIPTION OF THE DRAWINGS

The drawings show embodiments of the disclosed subject matter for the purpose of illustrating the invention. However, it should be understood that the present application is not limited to the precise arrangements and instrumentalities shown in the drawings, wherein.

DETAILED DESCRIPTION

Figure 1:
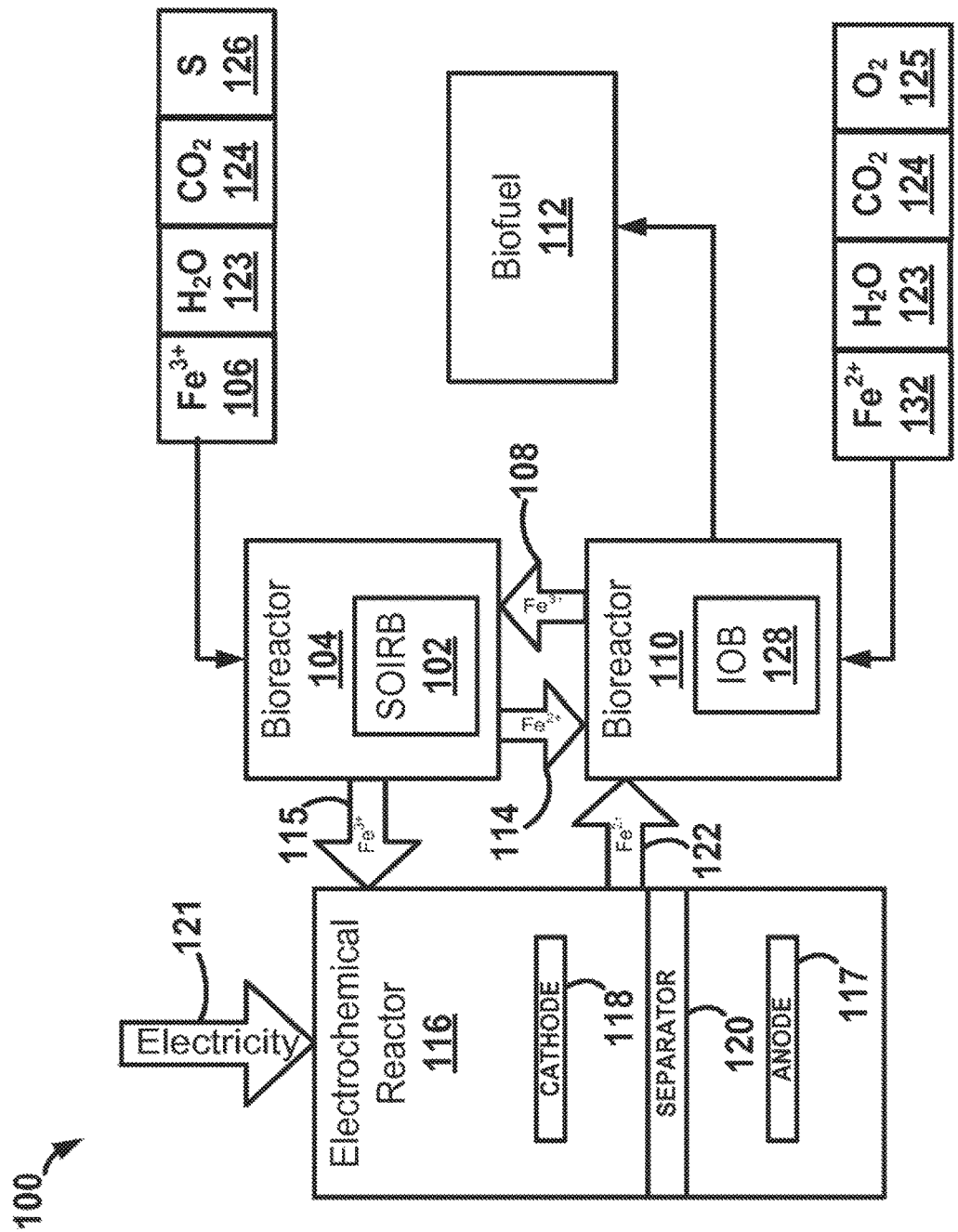
FIG. 1 a schematic diagram of systems according to some embodiments of the disclosed subject matter.
Figure 2:
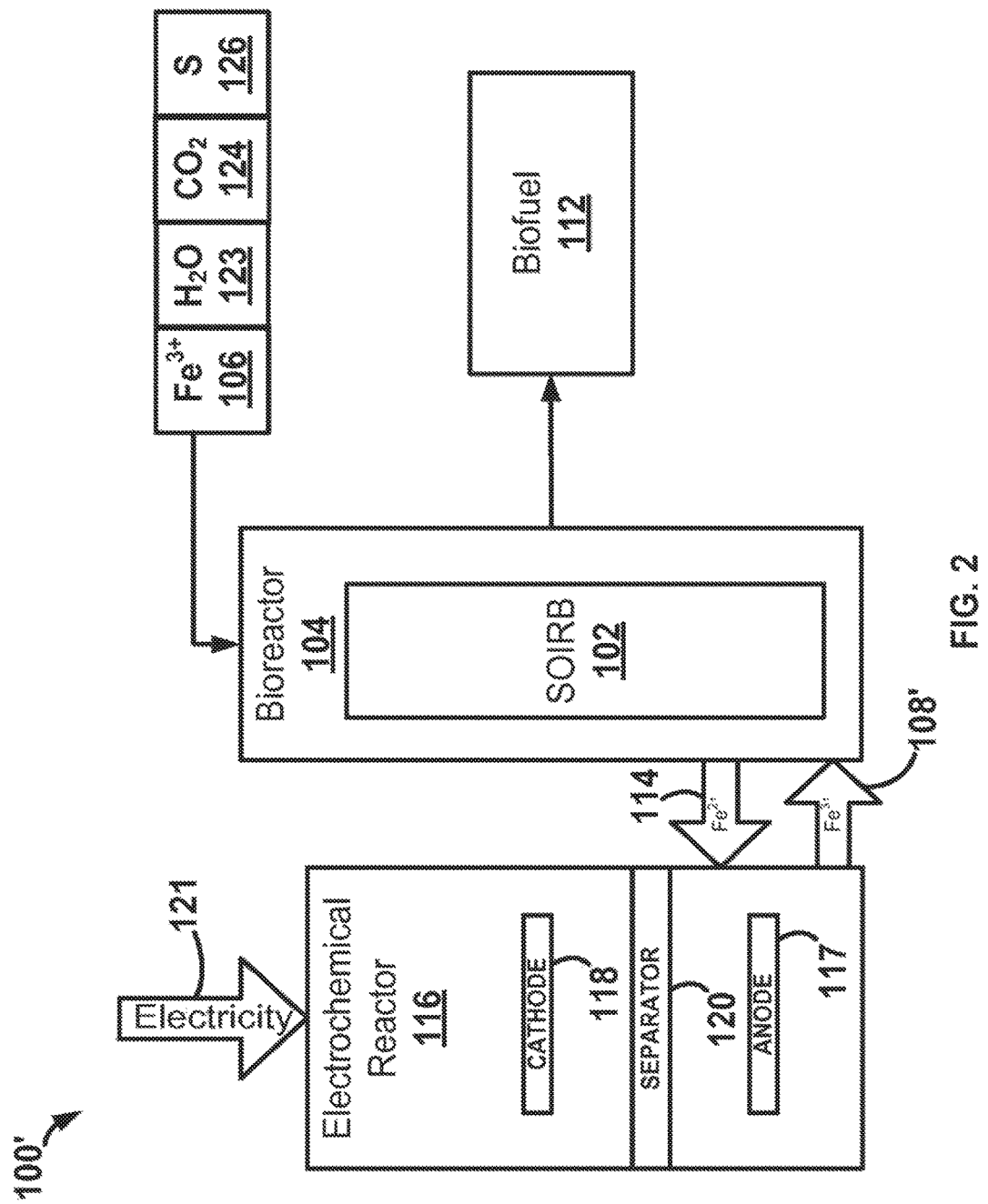
FIG. 2 a schematic diagram of systems according to some embodiments of the disclosed subject matter.

Referring now to FIGS. 1 and 2, aspects of the disclosed subject matter include methods and systems that include the application of chemolitotrophic sulfur oxidizing bacteria for concomitant carbon dioxide fixation, conversion of the carbon dioxide to a biofuel such as isobutanol, and oxidation of elemental sulfur to sulfate compounds. In some embodiments, ferric iron is simultaneously reduced back to ferrous iron and excess ferric iron is electrochemically reduced. Additional ferric iron can be added from other ferric iron-rich sources. Metabolic engineering is used to introduce a new pathway into the bacteria that starts with the precursors for amino acid synthesis to create butanols, e.g., isobutanol, etc.

Some embodiments include systems and methods for producing products such as biofuels and chemicals. As shown in FIG. 1, some embodiments include a system 100 for producing biofuels using genetically modified sulfur-oxidizing and iron-reducing bacteria (SOIRB) 102 grown in a first bioreactor 104 that are fed elemental sulfur, ferric iron, and carbon dioxide. The elemental sulfur is oxidized to sulfate providing electrons to the SOIRB, the carbon dioxide is used as a base material to be fixed into a biofuel or chemical, and the ferric iron functions as the ultimate electron acceptor and is reduced to ferrous iron. Initially, the ferric iron is typically provided from a first source 106 that is external to system 100, e.g., a ferric iron-rich stream in fluid communication with bioreactor 104. Typically, but not always, the ferric iron used in system 100 is substantially provided by a second source 108 that is generated in a second bioreactor 110. Second source 108 of ferric iron serves as a mediator for transferring electrons from SOIRB 102. In some embodiments, substantially all of the ferric iron used by bioreactor 104 is provided by a source external to system 100.

Bioreactor 104 includes SOIRB 102 that have been genetically modified to include a particular metabolic pathway to enable them to generate a biofuel 112. The operating parameters of bioreactor 104 are typically optimized to maximize the production of ferrous iron 114. Ferrous iron 114 is introduced to bioreactor 110. In some embodiments, bioreactor 104 will be configured so as to be fed about 70 mM to about 500 mM ferric iron. In some embodiments, the pH will likely be maintained in the range of about 1.5 to 4 and temperature at about 20 to 40 degrees Celsius. Methods and systems according to the disclosed subject matter have operating conditions that are optimized for optimal yield, conversion, etc. Bioreactors included in methods and systems according to the disclosed subject matter are typically operated in a continuous flow mode to maximize the conversion of the substrates to the products.

Excess ferric iron 115, which remains in bioreactor 104, is introduced to an electrochemical reactor 116, which is in fluid communication with the bioreactor. Electrochemical reactor 116 includes electrodes, i.e., an anode 117 and a cathode 118, a separator 120, and source of electrical energy 121. In some embodiments, cathode 118 is formed substantially from carbon and anode 117 is formed substantially from carbon and/or other known materials. In some embodiments, flow through or flow by porous electrodes are used. In some embodiments, separator 120 is a cation selective membrane, to allow for proton transfer across the membrane to achieve acid balance.

Electrochemical reactor 116 is typically configured to electrochemically reduce ferric iron 115 to a second source 122 of ferrous iron using source of electrical energy 121. In system 100, ferrous iron 114 will be continually regenerated back to ferric iron, i.e., second source 108, and the recycle loop can be theoretically closed without the need for additional ferric iron input from first source 106 beyond startup.

Some embodiments of the disclosed subject matter include systems having holding tanks for the ferrous iron rich streams and ferric iron rich streams to enable the electrochemical production of ferrous iron to operate independently of the bioreactor to take advantage of the transient pricing and availability of electricity. For example, at times during the day when electricity is least expensive, the electrochemical system would produce as much ferrous iron as possible to be stored and used slowly by the bioreactor, which will be operating continuously. This solves a major limitation encountered in photo bioreactors where interruptions in light can negatively impact the process.

System 100 includes a source of water 123, a source 124 of carbon dioxide, a source of oxygen 125, and a source of elemental sulfur 126—all except oxygen are in fluid communication with bioreactor 104 and all except sulfur are in fluid communication with bioreactor 110. In some embodiments, source 124 is carbon dioxide removed from air or energy plant emissions. In some embodiments, either in place of or in addition to carbon dioxide, carbonate, e.g., from mineral sources, is fed to bioreactor 104.

Second bioreactor 110 includes iron-oxidizing bacteria (IOB) 128 that have been genetically modified to include a particular metabolic pathway to enable them to generate a second particular biofuel (not shown) or biofuel 112. First and second sources 114, 122 of ferrous iron are in fluid communication with bioreactor 110. In some embodiments, a third source 132 of ferrous iron is also in fluid communication with bioreactor 110.

Referring now to FIG. 2, some embodiments include a system 100' that do not include second bioreactor 110. Instead, ferrous iron 114 produced in bioreactor 104 is directed to a side of electrochemical reactor 116 that includes anode 117 where it is oxidized to produce a second source or ferric iron 108', which is then recycled back to the bioreactor and fed to SOIRB 102.

Although not included in FIGS. 1 and 2, in some embodiments, systems 100 and 100' includes pumps for pumping the various constituents, into, through, and out of the system. In addition, the pumps are typically programmable to allow electrochemical reactor 116 to be turned off when the price of electricity is high and turned on when the price is low. Also, the pumps typically include a separator unit to separate one or more particular constituents that are to be pumped to other components of system 100 from the other constituents.

Figure 3:
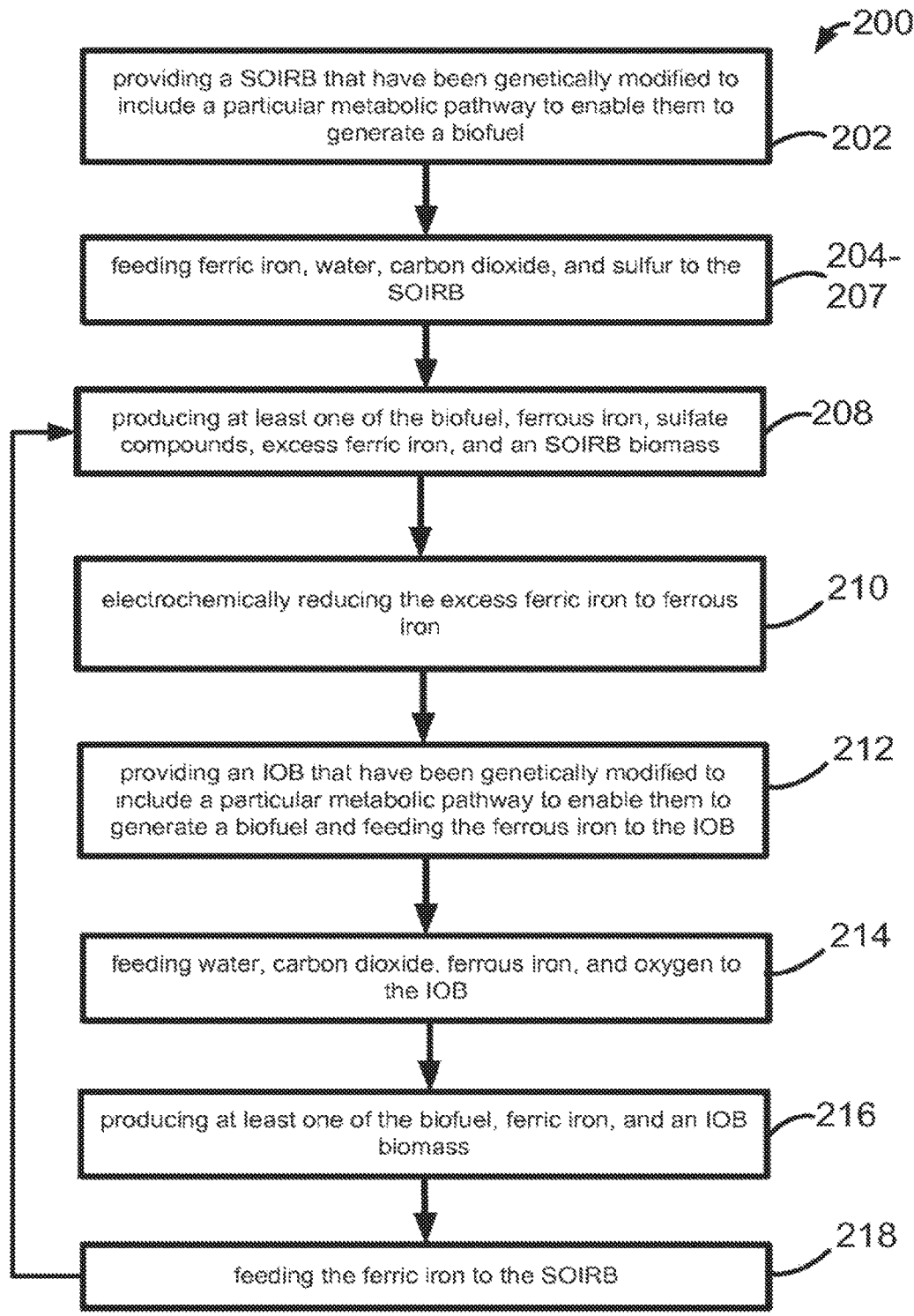
FIG. 3 is a chart of a method according to some embodiments of the disclosed subject matter.
Figure 4:
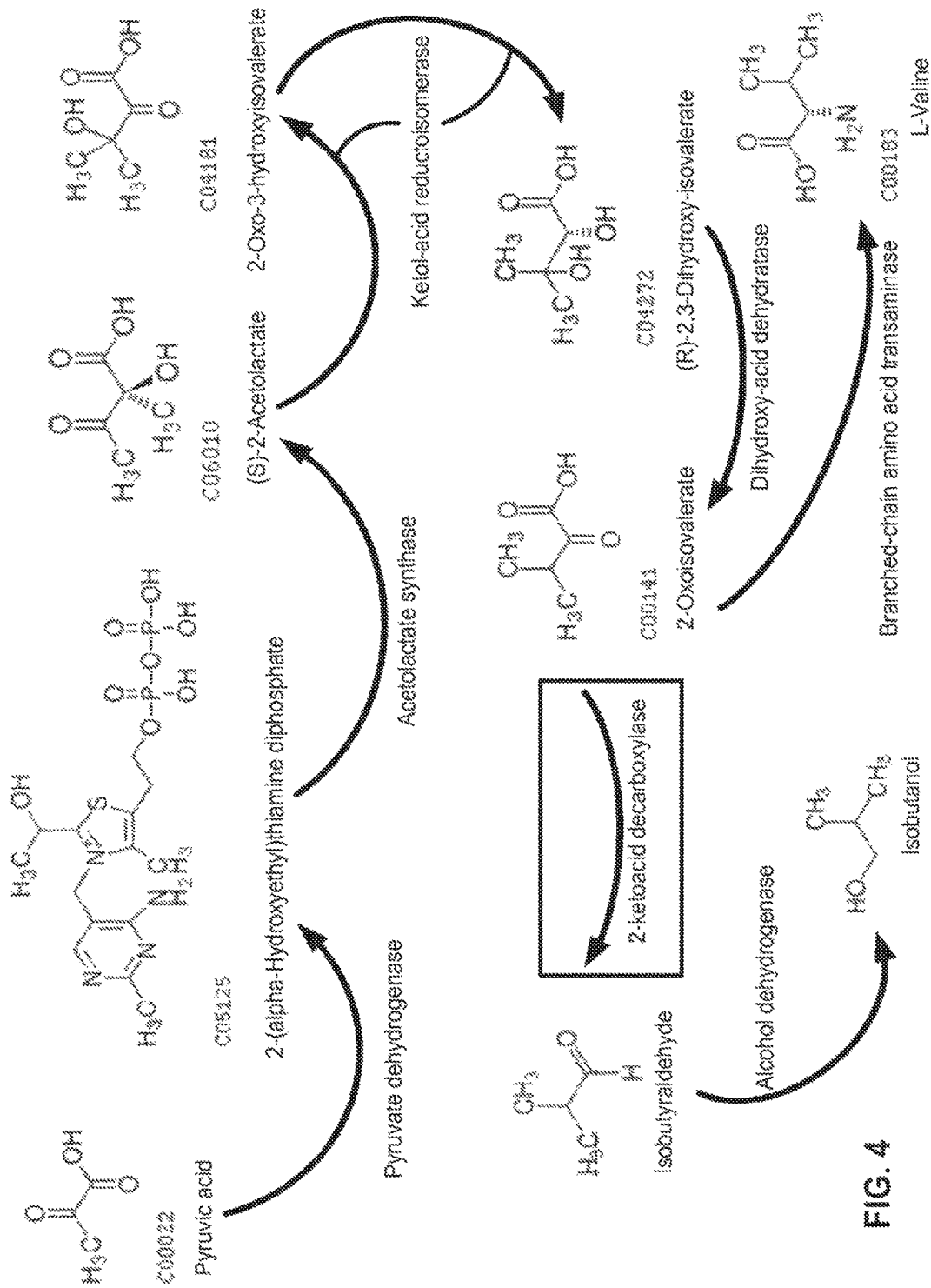
FIG. 4 is a diagram showing production of isobutanol via an oxidizing bacteria having a modified genetic sequence according to some embodiments of the disclosed subject matter.

Referring now to FIGS. 3 and 4, some embodiments include a method 200 for producing a biofuel using genetically modified sulfur-oxidizing and iron-reducing bacteria (SOIRB). As shown in FIG. 3, at 202, SOIRB that have been genetically modified to oxidize sulfur and reduce iron are provided.

As shown best in FIG. 4, in some embodiments, the SOIRB is substantially *A. ferrooxidans*, e.g., wild type *A. ferrooxidans* 23270 strain or similar, and the IOB are genetically modified by including at least one of a 2-keto-acid decarboxylase gene (outlined by box) and an alcohol dehydrogenase gene or similar. The production of isobutanol in prokaryotic hosts begins with the amino acid biosynthesis pathways. These pathways produce 2-keto acids, and these are converted to aldehydes using a 2-keto-acid decarboxylase. Alcohol dehydrogenase is then used to convert the aldehydes to alcohols.

In the case of isobutanol, the valine biosynthesis pathway is used, and the starting precursor is 2-keto-isovalerate.

In some embodiments, the SOIRB provided are genetically modified to be able to utilize hydrogen as an electron donor. The use of hydrogen as a mediator improves system efficiency because hydrogen may be cogenerated with ferrous iron during the electrochemical regeneration step. There are various hydrogenase enzymes from different organisms that can be used in microbial biohydrogen production. But other hydrogenase enzymes, found in organisms such as Metallosphaera sedula and hodopseudomonas palustris, enable hydrogen uptake and its use as a reductant. Of course, because *A. ferrooxidans* also contains its own hyddrogenase that can be used as described here, in some embodiments, the SOIRB provided are not genetically modified to be able to utilize hydrogen as an electron donor.

Referring again to FIG. 3, at 204, a first source of ferric iron is fed to the SOIRB. At 205, water is fed to the IOB. At 206, carbon dioxide is fed to the IOB. At 207, elemental sulfur is fed to the SOIRB. At 208, ferrous iron, sulfate compounds, excess ferric iron, and an SOIRB biomass are produced. In some embodiments, ferrous iron production is maximized during 208. During 208, elemental sulfur is oxidized and ferric iron is reduced. At 210, the excess ferric iron remaining is electrochemically reduced to a second source of ferrous iron. Hydrogen is also often produced while electrochemically reducing the ferric iron. Next, at 212, iron-oxidizing bacteria (IOB) that have been genetically modified to include a particular metabolic pathway to enable them to generate a second particular biofuel are provided. Still at 212, the second source of ferrous iron and the hydrogen are fed to the IOB. The second source of ferrous iron serves as a mediator for transferring electrons to the IOB. At 214, water, carbon dioxide, the first source of ferrous iron, and oxygen are fed to the IOB. At 216, a particular biofuel, a second source of ferric iron, and an IOB biomass are produced. In some embodiments, the biofuel is one of isobutanol, a long chain alcohol, or an alkane. At 218, the second source of ferric iron is fed to the SOIRB and the process returns to 208 where additional biofuel, ferrous iron, sulfate compounds, excess ferric iron, and an SOIRB biomass are produced.

Figure 5:
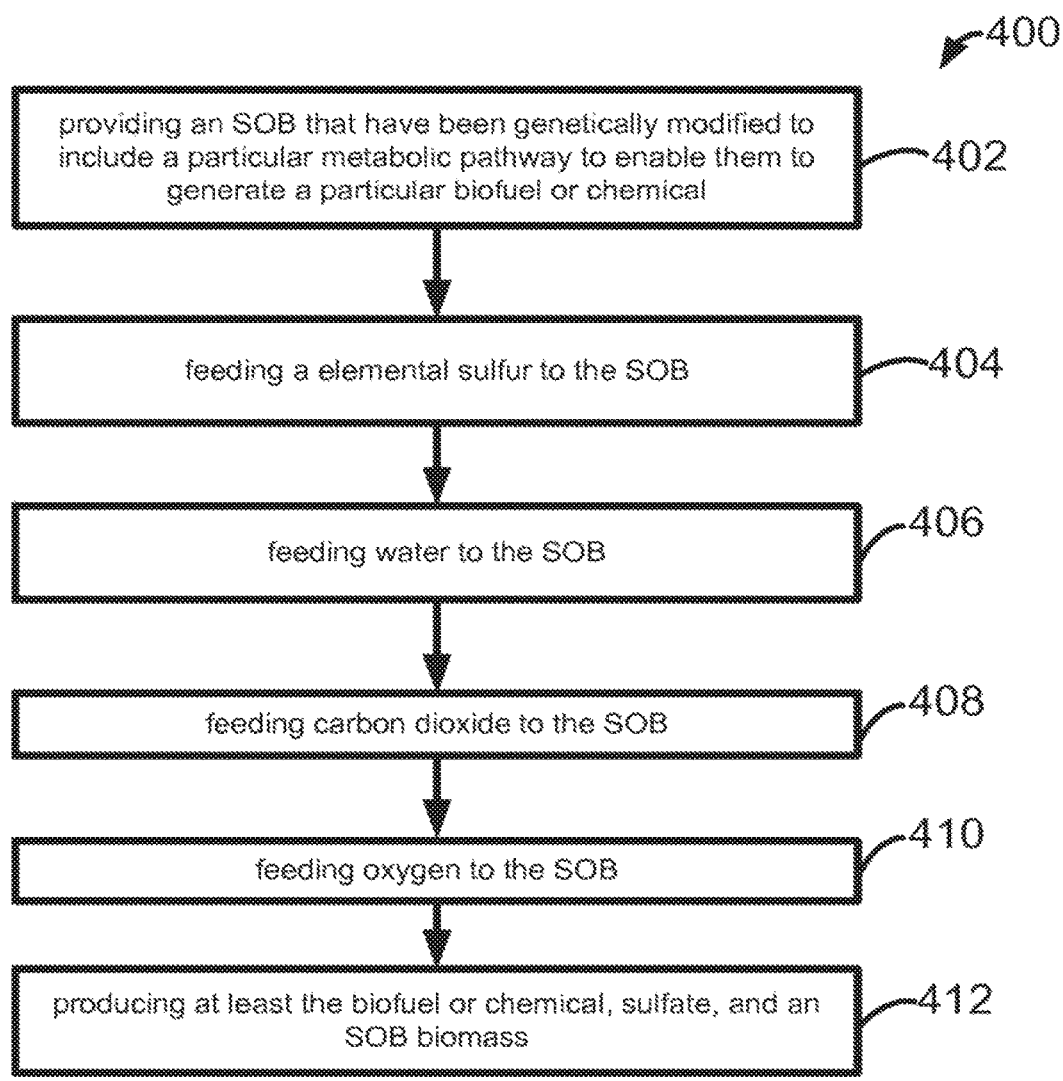
FIG. 5 is a chart of a method according to some embodiments of the disclosed subject matter.

Referring now to FIG. 5, some embodiments include a method 400 for producing a chemical or biofuel using genetically modified sulfur-oxidizing bacteria (SOB). At 402, SOB that have been genetically modified to include a particular metabolic pathway to enable them to generate a first particular biofuel or chemical are provided. At 404, elemental sulfur is fed to the SOB. At 406, water is fed to the SOB. At 408, carbon dioxide is fed to the SOB. At 410, oxygen is fed to the SOB. At 412, a biofuel or chemical, sulfate, and an SOB biomass are produced. In some embodiments, the chemical is one of a commodity chemical, a specialty chemical, a feedstock such as an acid, an amino acid, a carbohydrate, or a combination thereof. At 412, elemental sulfur is oxidized.

Reverse microbial fuel cells according to the disclosed subject matter utilize carbon dioxide and electrical input to produce infrastructure compatible transportation fuels. The technology uses cultures of IOB, e.g., *A. ferrooxidans*, which are genetically modified to produce isobutanol.

Systems and methods according to the disclosed subject matter use only abundant, inexpensive redox mediators. They do not use costly rare earth elements or organic redox shuttles, and thus can be potentially deployed economically at scale. They potentially exceed an overall efficiency greater than one percent and butanol has desirable fuel properties and is compatible with transportation-fuel infrastructure.

Although the disclosed subject matter has been described and illustrated with respect to embodiments thereof, it should be understood by those skilled in the art that features of the disclosed embodiments can be combined, rearranged, etc., to produce additional embodiments within the scope of the invention, and that various other changes, omissions, and additions may be made therein and thereto, without parting from the spirit and scope of the present invention.

What is claimed is:

1. A system for producing isobutanol from genetically modified sulfur-oxidizing and iron-reducing bacteria (SOIRB) and iron oxidizing bacteria (IOB), said system comprising:
a first bioreactor comprising sulfur-oxidizing and iron-reducing bacteria (SOIRB), wherein said SOIRB comprises a valine biosynthesis metabolic pathway that produces 2-keto acids and is genetically modified to include a 2-keto-acid decarboxylase gene and an alcohol dehydrogenase gene, said SOIRB being genetically modified so that said genes in said SOIRB convert said 2-keto acids to isobutanol;
a first source of ferric iron in fluid communication with said first bioreactor;
a first source of ferrous iron produced by said first bioreactor, said first bioreactor configured to feed said first source of ferrous iron to a second bioreactor, said second bioreactor comprising iron oxidizing bacteria (IOB), wherein said IOB comprises a valine biosynthesis metabolic pathway that produces 2-keto acids and is genetically modified to include a 2-keto-acid decarboxylase gene and an alcohol dehydrogenase gene, said IOB being genetically modified so that said genes in said IOB convert said 2-keto acids to isobutanol; and
a second source of ferric iron produced by said second bioreactor, said second bioreactor configured to feed said second source of ferric iron to said first bioreactor.

2. The system of claim 1, further comprising an electrochemical reactor in fluid communication with said first bioreactor and said second bioreactor, wherein said electrochemical reactor is configured to directly reduce excess ferric iron provided by said first bioreactor to a second source of ferrous iron and to generate a stream comprising said second source of ferrous iron to be fed to said second bioreactor.

3. The system of claim 2, wherein said electrochemical reactor includes a cathode formed from at least one of nickel and glassy carbon.

4. The system of claim 1, further comprising:
a source of water in fluid communication with said first bioreactor;
a source of sulfur in fluid communication with said first bioreactor; and
a source of carbon dioxide in fluid communication with said first bioreactor;
a source of oxygen in fluid communication with said second bioreactor;
a source of carbon dioxide in fluid communication with said second bioreactor;
and a third source of ferrous iron in fluid communication with said second bioreactor.

5. The system of claim 1, wherein said SOIRB are genetically modified with a hydrogenase enzyme to be able to utilize hydrogen as an electron donor.

6. The system of claim 1, wherein said SOIRB is *Acidithiobacillus ferrooxidans*.

7. The system of claim 1, wherein said IOB is *Acidithiobacillus ferrooxidans*.

8. A method for producing isobutanol from genetically modified bacteria, said method comprising:
providing the system of claim 1;
feeding said first source of ferric iron to said first bioreactor comprising said SOIRB; feeding sulfur, water, and carbon dioxide to said first bioreactor comprising said SOIRB; growing said SOIRB under conditions to oxidize said sulfur and to reduce said first source of ferric iron to produce said isobutanol, said first source of ferrous iron, sulfate, excess ferric iron, and an SOIRB biomass; and
feeding said first source of ferrous iron to said second bioreactor comprising said IOB.

9. The method of claim 8, further comprising:
feeding water, carbon dioxide, and oxygen to said second bioreactor comprising said IOB;
growing said IOB under conditions to produce said isobutanol, said second source of ferric iron, and an IOB biomass; and
feeding said second source of ferric iron to said first bioreactor comprising said SOIRB.

10. The method of claim 9, further comprising:
electrochemically reducing said excess ferric iron to a second source of ferrous iron; and feeding said second source of ferrous iron to said second bioreactor comprising said IOB.

11. The method of claim 8, wherein said SOIRB are genetically modified with a hydrogenase enzyme to be able to utilize hydrogen as an electron donor.

12. The method of claim 8, further comprising:
feeding a third source of ferrous iron to said second bioreactor comprising said IOB.

13. The method of claim 8, wherein said SOIRB is *Acidithiobacillus ferrooxidans*.

14. The method of claim 8, wherein said IOB is *Acidithiobacillus ferrooxidans*.

* * * * *